(12) United States Patent
Belotserkovsky (10) Patent No.: US 7,486,976 B1
(45) Date of Patent: Feb. 3, 2009

(54) OPTICAL NON-INVASIVE BLOOD MONITORING SYSTEM AND METHOD

(76) Inventor: Edward Belotserkovsky, 2939 20th Ave., San Francisco, CA (US) 94132

(*) Notice: Subject to any disclaimer, the term of this patent is extended or adjusted under 35 U.S.C. 154(b) by 296 days.

(21) Appl. No.: 11/492,451

(22) Filed: Jul. 25, 2006

(51) Int. Cl.
*A61B 5/1455* (2006.01)

(52) U.S. Cl. .................................. 600/310; 600/316

(58) Field of Classification Search ............ 600/309, 600/310, 316, 322, 323
See application file for complete search history.

(56) References Cited

U.S. PATENT DOCUMENTS

| | | | |
|---|---|---|---|
| 4,679,936 A | | 7/1987 | Gerharz |
| 5,692,504 A | * | 12/1997 | Essenpreis et al. .......... 600/316 |
| 5,741,211 A | | 4/1998 | Renirie et al. |
| 5,795,394 A | | 8/1998 | Belotserkovsky et al. |
| 5,823,966 A | | 10/1998 | Buchert |
| 6,088,605 A | | 7/2000 | Griffith et al. |
| 6,088,606 A | | 7/2000 | Ignotz et al. |
| 6,113,578 A | | 9/2000 | Brown |
| 6,122,536 A | | 9/2000 | Sun et al. |
| 6,219,565 B1 | | 4/2001 | Cupp et al. |
| 6,226,082 B1 | | 5/2001 | Roe |
| 6,313,914 B1 | | 11/2001 | Roe |
| 6,427,088 B1 | | 7/2002 | Bowman, IV et al. |
| 6,442,410 B1 | | 8/2002 | Steffes |
| 6,505,059 B1 | | 1/2003 | Kollias et al. |
| 6,618,138 B2 | | 9/2003 | Khoury |
| 6,650,915 B2 | | 11/2003 | Routt et al. |
| 6,675,030 B2 | | 1/2004 | Ciurczak et al. |
| 6,721,582 B2 | | 4/2004 | Trepagnier et al. |
| 6,723,048 B2 | | 4/2004 | Fuller |
| 6,804,544 B2 | | 10/2004 | Van Antwerp et al. |
| 6,816,841 B1 | | 11/2004 | Suginuma |
| 6,827,702 B2 | | 12/2004 | Lebel et al. |
| 6,836,337 B2 | | 12/2004 | Cornsweet |
| 6,949,070 B2 | | 9/2005 | Ishler |
| 6,999,808 B2 | | 2/2006 | Gobeli et al. |
| 7,024,245 B2 | | 4/2006 | Lebel et al. |
| 2001/0035950 A1 | | 11/2001 | Nicholas |
| 2002/0016534 A1 | | 2/2002 | Trepagnier et al. |
| 2003/0233036 A1 | | 12/2003 | Ansari et al. |
| 2004/0204673 A1 | | 10/2004 | Flaherty |
| 2005/0137469 A1 | | 6/2005 | Berman et al. |

OTHER PUBLICATIONS

Loginov et al., "Fiber optic devices of data collecting and processing" Novosibirsk, "Nauka," Siberian Branch, USSR 1991.
Maier et al., "Possible correlation between blood glucose concentration and reduced scattered coefficient of tissues in the near infrared," Optics Letters, Dec. 15, 1994, V.19, 24.

* cited by examiner

*Primary Examiner*—Eric F Winakur
*Assistant Examiner*—Etsub D Berhanu
(74) *Attorney, Agent, or Firm*—Cascio Schmoyer & Zervas (57) ABSTRACT

A simple noninvasive technique that is capable of very accurate and fast blood analyte, e.g., glucose, level monitoring is provided. Fluctuation in the levels of glucose and other analytes affect the refractive index of blood and extra cellular fluid in biological tissue. Given that the propagation speed of light through a medium depends on its refractive index, continuous monitoring of analyte levels in tissue is achieved by measuring characteristics of the tissue that can be correlated to the refractive index of the tissue. For instance, the frequency or number of optical pulse revelations that are transmitted through an individual's tissue of known thickness within a certain time period can be correlated to an individual's blood glucose level.

27 Claims, 4 Drawing Sheets

OPTICAL NON-INVASIVE BLOOD MONITORING SYSTEM AND METHOD

FIELD OF THE INVENTION

The present invention is directed to instruments and methods for performing non-invasive measurements of analyte concentrations and for monitoring, analyzing and regulating tissue status, such as tissue glucose levels.

BACKGROUND OF THE INVENTION

Diabetes is a chronic life threatening disease for which there is presently no cure. It is the fourth leading cause of death by disease in the United States and over a hundred million people worldwide are estimated to be diabetic. Diabetes is a disease in which the body does not properly produce or respond to insulin. The high glucose concentrations that can result from this affliction can cause severe damage to vital organs, such as the heart, eyes and kidneys.

Type I diabetes (juvenile diabetes or insulin-dependent diabetes mellitus) is the most severe form of the disease, comprising approximately 10% of the diabetes cases in the United States. Type I diabetics must receive daily injections of insulin in order to sustain life. Type II diabetes, (adult onset diabetes or non-insulin dependent diabetes mellitus) comprises the other 90% of the diabetes cases. Type II diabetes is often manageable with dietary modifications and physical exercise, but may still require treatment with insulin or other medications. Because the management of glucose to near-normal levels can prevent the onset and the progression of complications of diabetes, persons afflicted with either form of the disease are instructed to monitor their blood glucose concentration in order to assure that the appropriate level is achieved and maintained.

Traditional methods of monitoring the blood glucose concentration of an individual require that a blood sample be taken daily. This invasive method can be painful, inconvenient, and expensive, pose the risk of infection and does not afford continuous monitoring. So-called semi-invasive (or less-invasive) methods require an individual to take samples through the skin but the techniques do not puncture blood vessels. Most semi-invasive glucose monitoring devices measure the concentration of glucose that is present in the interstellar fluid that is between the skin's surface and underlying blood vessels. The devices could be implanted to provide continuous (real time) glucose level monitoring but individuals would have to undergo implantation surgery. Moreover, once implanted the devices are often inaccessible for maintenance.

Another glucose measuring method involves urine analysis, which, aside from being inconvenient, may not reflect the current status of the patient's blood glucose because glucose appears in the urine only after a significant period of elevated levels of blood glucose. An additional inconvenience of these traditional methods is that they require testing supplies such as collection receptacles, syringes, glucose measuring devices and test kits. Although disposable supplies have been developed, they are costly and can require special methods for disposal.

Many attempts have been made to develop a painless, non-invasive external device to monitor glucose concentrations. The various approaches have included electrochemical and spectroscopic technologies, such as near-infrared spectroscopy and Raman spectroscopy. These systems measure blood glucose concentration based on IR blood absorption and emission at selected wavelengths. A major problem with these non-invasive optical techniques is that blood glucose absorption in the near, mid or far IR regions is very weak. Compounding this problem is the fact that water, proteins, fat, and other tissue components tend to blur the glucose fingerprint and thereby attenuate the detectable signals and as a result these blood glucose monitoring devices are not very accurate. Techniques used to compensate for the poor signals and the related signal-to-noise problems including complicated spectral analysis and processing instrumentation have not been successful. Thus, despite extensive efforts, none of these methods has, so far, yielded a non-invasive device or method for the in vivo measurement of glucose that is sufficiently accurate, reliable, convenient and cost-effective for routine use.

SUMMARY OF THE INVENTION

The present invention is based in part on the recognition that glucose levels affect the refractive index of blood and extra cellular fluid. Biological tissue is a very complex composition and, as used herein, the phrase "refractive index of tissue" refers to a composite or collective refractive index that is derived from the different refractive indices of the various materials that are present in the tissue being monitored. Given that the propagation speed of light through a medium v depends on its refractive index n, as $v=c/n$, where c is the speed of light in vacuum, it is possible to continuously monitor glucose levels in tissue by measuring characteristics of the tissue that can be correlated to the refractive index of the tissue and to the speed at which electromagnetic radiation travels through the tissue.

For instance, with the present invention, the frequency or number of optical pulse revelations that are transmitted through tissue of known thickness within a certain time period can be correlated to the individual' blood glucose level. Thus, the invention provides a simple design that is capable of very accurate and fast blood glucose level monitoring.

In one aspect, the invention is directed to a device for noninvasive measurement of the levels of at least one analyte in a subject that includes:
  means for irradiating the subject through tissue with electromagnetic radiation;
  means for detecting the radiation that passes through the tissue;
  means for calculating the speed at which the electromagnetic radiation passes through the tissue, such as a device that measures the frequency or the number of optical pulse revelations through the tissue;
  means for correlating the calculated speed of the electromagnetic radiation, as measured for example by the frequency or number of optical pulse revelations, to the concentration of the at least one analyte in the subject.

In another aspect, the invention is directed to a device for noninvasive measurement of the levels of glucose in a subject that includes:
  means for irradiating the subject through tissue with electromagnetic radiation having a wavelength such that the speed of the electromagnetic radiation traversing through the tissue is sensitive to the glucose concentration in the tissue;
  means for detecting the radiation that passes through the tissue;
  means for calculating the speed at which the electromagnetic radiation passes through the tissue such as a device that measures the frequency or number of optical pulse revelations through the tissue;

means for correlating the calculated speed of the electromagnetic radiation, as measured for example by the frequency or number of optical pulse revelations, to the concentration of glucose in the subject.

It should be noted that the means for irradiating the subject through tissue with electromagnetic radiation does not need to generate pulses at regular intervals.

In a further aspect, the invention is directed to a noninvasive method of monitoring the levels of at least one analyte (e.g., glucose) in a subject that includes:
(a) irradiating the subject through tissue of known thickness with electromagnetic radiation;
(b) detecting the radiation that passes through the tissue;
(c) calculating the speed at which the electromagnetic radiation passes through the tissue such as by measuring the frequency or number of optical pulse revelations;
(d) correlating the calculated speed of the electromagnetic radiation, as measured for example by the frequency or number of optical pulse revelations, to the concentration of the at least one analyte (e.g., glucose) in the subject.

While the invention will be illustrated with glucose, it is understood that the invention provides the ability to achieve continuous monitoring and control of other blood constituents or analytes such as, for example, cholesterol, triglycerides, urea, amino acids, and proteins, e.g., albumin and enzymes.

DETAILED DESCRIPTION OF THE PREFERRED EMBODIMENTS

Figure 1:
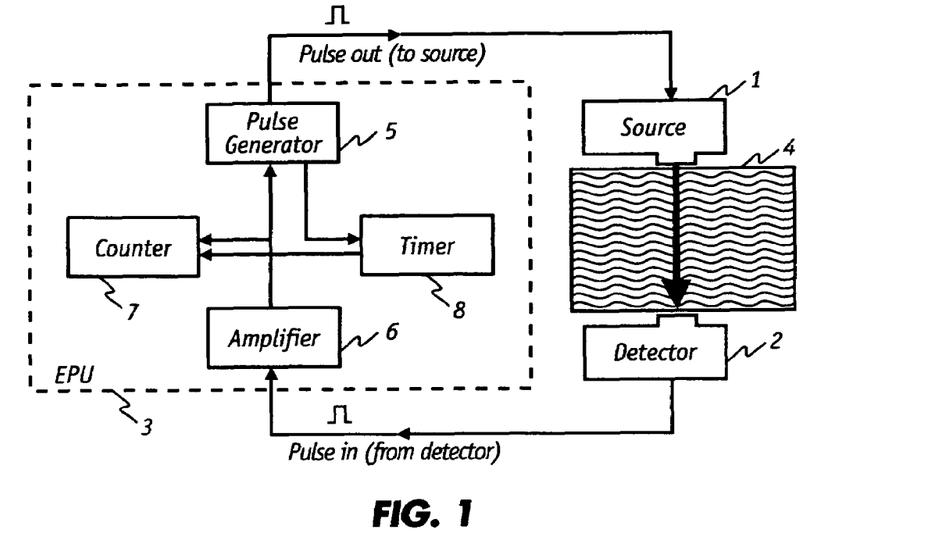
FIGS. 1, 4, and 5 are schematics of alternative configurations of non-invasive glucose level monitoring instruments.

As shown in FIG. 1, the glucose monitoring device includes an optical or light source of electromagnetic radiation 1 and detector 2 which, are connected to an electronic processing unit (EPU) 3. EPU 3, which includes an electrical pulse generator 5, amplifier 6, counter 7 and timer 8 is capable of generating, amplifying and counting electronic pulses and monitoring time precisely. Source 1 and detector 2 are preferably disposed on opposite sides of glucose-containing tissue 4, which is to be monitored.

Optical source 1 can comprise any suitable conventional source such as, for sample, a laser, a laser diode, a light emitting diode (LED), or some other type of light emitting device that is capable of generating light in a relatively narrow wavelength band in a high frequency pulse regime. The intensity should be sufficient to transmit through tissue being monitored but the intensity and energy levels of the radiation must not be hazardous to the tissue. The radiation is preferably within the ultra-violet (UV), visible, infrared radiation (IR), and radio frequency (RF) ranges. The light source 1 could also comprise a broadband light source such as a white light LED. Such a broadband light source can also be paired with one or more optical filters that are designed to pass only specific wavelength bands of light. Light source 1 can also include appropriate optics that collimates and directs a beam of radiation into tissue 4.

Detector 2 can comprise a photodetector or any other type of device capable of high speed sensing the light that is transmitted through tissue 4. The detector 2 could be configured to sense the intensity of one or more particular wavelength bands. Suitable optics can be employed to collect and focus the transmitted radiation into the detector. The EPU can be built using separate components or it can design as an integrated microchip that supports several measurement channels.

For testing purposes, the glucose monitoring device can be calibrated by using an aqueous solution that contains the appropriate amounts of glucose, salts, proteins and other ingredients that are sufficient to simulate the tissue that would be monitored.

In operation, tissue 4 is positioned between source 1 and detector 2 of the glucose monitoring device such that the thickness of the tissue through which radiation passes remains relatively constant during the monitoring process. Once tissue 4 is secured, the device is activated so that pulse generator 5 produces an initial single electrical pulse to optical source 1, in addition, pulse generator 5 simultaneously signals timer 8 to begin its timing mechanism. Upon receiving the single electrical pulse, optical source 1 generates an optical pulse, which propagates through the monitored tissue 4. When the optical pulse reaches detector 2, the detector generates an electrical pulse to amplifier 6 which in turn commands counter 7 to register a pulse revelation and signals pulse generator 5 to generate another single electrical pulse. Thereupon, pulse generator 5 immediately generates a second single pulse to optical source 1 and the process of registering the circulating pulses is repeated. At the lapsed of a pre-selected and installed time duration, timer 8 sends a signal to counter 7 to record the number of pulse revelations that were registered during the preceding time interval. In the meantime, pulse generator 5 continues to generate a second set of pulses for a new measurement sequence. As further described herein, for this glucose monitoring device which operates in the pulse measuring mode, the number of pulses registered within a prescribed time frame is proportional to the glucose concentration in the tissue and by gauging the changes in this pulse circulation frequency, fluctuations in the individual's glucose concentration can be measured. With the inventive technique, it is possible to circulate and detect a large number of pulse propagations through the tissue even in a relatively short period of time, with each monitored pulse contributing to the final glucose concentration measurement. The precision and high sensitivity exhibited by the invention are attributable, in part, to the fact that the large number of readings minimize the adverse effects that are contributed by aberrations and fluctuations caused by noise and other extraneous factors.

The relationship between the number N of pulse circulations measured within a time period t is expressed as follows:

$$N = \frac{t}{\frac{\text{Ln}}{c} + \Delta\tau} = \frac{t}{\frac{L}{v} + \Delta\tau}; \qquad (1)$$

where L is the thickness of the monitored tissue, n is the tissue's refractive index, c is the speed of light in vacuum, v=c/n is the propagation speed of the pulse in the tissue, and $\Delta\tau$ is the time delay in the EPU. (See, A. V. Loginov et al., "Fiber optic devices of data collecting and processing," Novosibirsk, "Nauka," Siberian Branch, 1991.) Similarly, the dependence of the tissue refractive index n on the glucose concentration in the tissue can be presented as:

$$n(\lambda, C) = n_0(\lambda) + k(\lambda)*C; \qquad (2)$$

where $n_0(\lambda)$ is the refractive index of the tissue without glucose, $k(\lambda)$ is the refractive index sensitivity to glucose concentration, and C is the blood glucose concentration. Applying the relationship of equation (2), for a given radiation of wavelength $\lambda$, the correlation between the number (or frequency) N(C) of registered pulse circulations and the glucose concentration C can be expressed as:

$$N(C) = \frac{t}{\frac{L \cdot (n_0(\lambda) + k(\lambda)*C)}{c} + \Delta\tau}; \qquad (3)$$

and as a corollary, the relationship between the changes in the frequency of registered pulse circulations to glucose concentration becomes:

$$\Delta N(C) = N(0) - N(C) = \qquad (4)$$
$$\frac{L \cdot k(\lambda) \cdot C \cdot t \cdot c}{[L \cdot (n_0 + k \cdot C) + \Delta\tau \cdot c] \cdot [L \cdot n_0 + \Delta\tau \cdot c]} \approx \frac{L \cdot k(\lambda) \cdot C \cdot t \cdot c}{[L \cdot n_0 + \Delta\tau \cdot c]^2};$$

where N(0) is the frequency of the pulse circulation when the glucose concentration C=0. As is apparent, by monitoring the changes in the pulse circulation frequency (PCF), the invention enables detection of extremely small fluctuations in the glucose concentration within the tissue. The sensitivity S(C) of the device to the glucose concentration can be expressed as:

$$S(C) = \frac{d(\Delta N(C))}{dC} \cong \frac{L \cdot k(\lambda) \cdot t \cdot c}{[L \cdot n_0 + \Delta\tau \cdot c]^2}. \qquad (5)$$

Analysis of equation (5) shows that the glucose monitoring device sensitivity is directly proportional to the measurement time interval t and inversely proportional to the monitored tissue thickness L and EPU time delay, $\Delta\tau$. The sensitivity is independent of the glucose concentration level in the tissue, which is consistent with the linear nature of the relationship between glucose monitor output signal (pulse circulation frequency) and the glucose concentration level.

Figure 2:
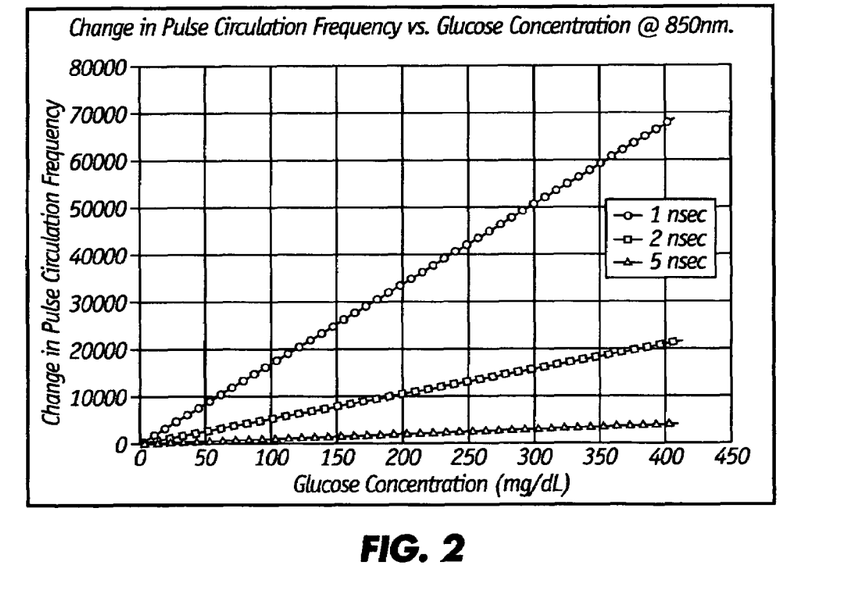
FIG. 2 is a graph showing the change in pulse circulation frequency vs. glucose concentration measured with a glucose monitoring device using radiation with a wavelength of 850 nm.

A simulation of a glucose monitoring device employing radiation with a wavelength of 850 nm in measuring glucose levels in a tissue with thickness L of 0.05 m was conducted to illustrate the effects of the EPU time delay. At a wavelength $\lambda$ of 850 nm, for equation (2), the refractive index sensitivity to the glucose concentration, $k(\lambda)=1.515*10^{-6}$ (dL/mg) and $n_0(\lambda)=1.325$. (See, J. S. Maier, et. al. "Possible Correlation between Blood Glucose Concentration and Reduced Scattering Coefficient of Tissues in the Near-Infrared," Optics Letters, Vol. 19, No. 24, pp. 2062-2064, Dec. 15, 1994.) FIG. 2 is a graph depicting the change in pulse circulation frequency (that is, the output pulse circulation frequency $\Delta N(C)$) as a function of glucose concentration in the tissue when measured at three different EPU delay times of 1, 2, and 5 nanoseconds. As is apparent, the pulse circulation frequency $\Delta N(C)$ has a linear relationship with the blood glucose level. The linear character of the output signal (pulse circulation frequency) and the device's ability to exhibit constant sensitivity throughout the measurement range are important design criteria. Moreover, given that the glucose concentration is reflected in the changes of the pulse circulation frequency, it is not necessary to calibrate the device against the glucose measurement range for an individual.

Figure 3:
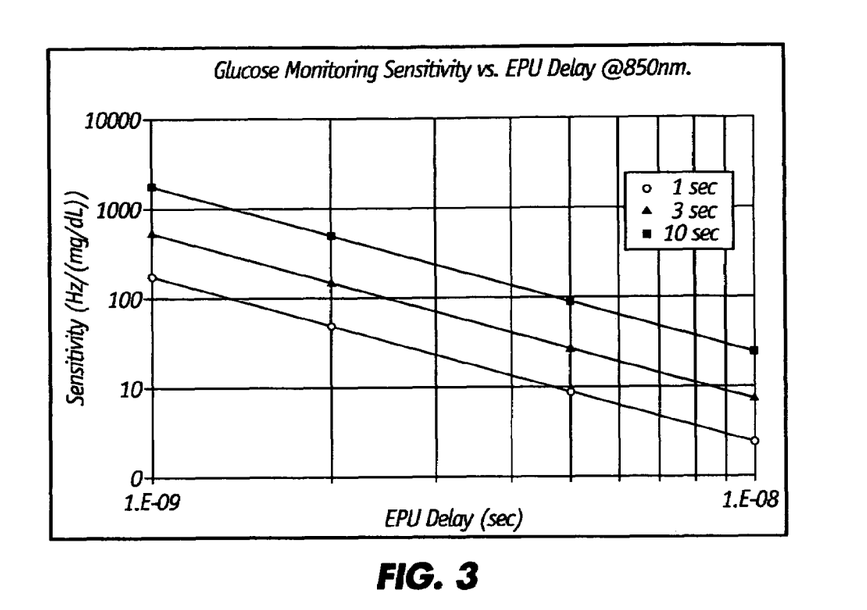
FIG. 3 is a graph showing the sensitivity of a glucose monitoring device vs. electronic processing unit (EPU) time delay.

A simulation of a glucose monitoring device employing radiation with a wavelength of 850 nm for measuring glucose levels in a tissue with a thickness L of 0.05 m was conducted to illustrate the effects of the measurement time interval. FIG. 3 is a graph of the glucose monitoring sensitivity as a function of EPU delay time as measured at three different measurement time intervals of 1, 3, and 10 seconds. The data shows that using longer measurement time intervals increases the sensitivity and resolution. As is apparent from the graph, the inventive glucose monitoring technique exhibits extremely high sensitivity and thus is capable of very accurate real time blood glucose level measurements. The sensitivity data also demonstrate that the inventive glucose monitoring device is capable of extremely high resolution. For example, when a device is operated at a 1 second measurement duration time, a pulse circulation frequency of $10^8$ Hz (which corresponds to an EPU delay time of about $10^{-8}$ s), and an assumed counter frequency error of about $10^{-1}$ Hz, the glucose monitoring device is expected to exhibit a resolution of about 0.05 mg/dL.

With regard to sensitivity, a device reaches its theoretical limit when $\Delta\tau=0$:

$$S(C) \cong \frac{k(\lambda) \cdot t \cdot c}{L \cdot n_0^2}. \qquad (6)$$

Thus, for example, when a glucose monitoring device that is operating at a wavelength $\lambda$ of 850 nm so that the refractive index sensitivity to the glucose concentration $k(\lambda)=1.515*10^{-6}$ (dL/mg) and $n_0(\lambda)=1.325$ is used to monitor tissue with a thickness L of 0.05 m, and $c=3*10^8$ m/s, the theoretical limit of the device sensitivity contains $S_{th}(C) = 4.5*10^3$ Hz/(mg/dL) when the measurement time interval t is 1 second.

Figure 4:
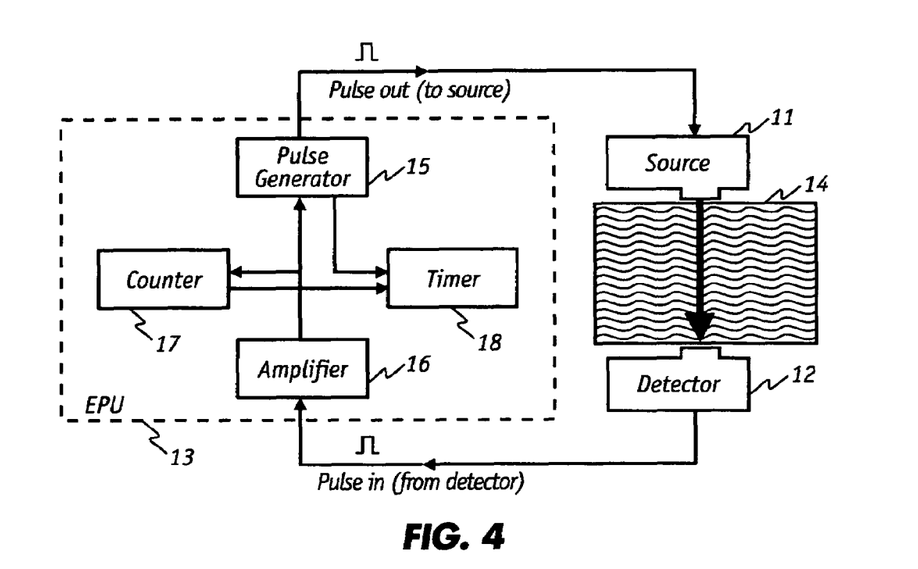

FIG. 4 illustrates another embodiment of the glucose monitoring device in which blood glucose levels are monitored in the time measuring mode which means that the time interval necessary for the circulation of a defined number of pulses is the measure of the glucose level. As shown, this glucose monitoring device includes an optical or light source of electromagnetic radiation 11 and detector 12 which are connected to electronic processing unit (EPU) 13. EPU 13, which includes an electrical pulse generator 15, amplifier 16, counter 17 and timer 18 is capable of generating, amplifying and counting electronic pulses and monitoring time precisely. Source 11 and detector 12 are preferably disposed on opposite sides of glucose-containing tissue 14, which is to be monitored.

In operation, tissue 14 is positioned between source 11 and detector 12 such that the thickness of the tissue through which radiation passes remains relatively constant during the monitoring process. Once tissue 14 is secured, the device is activated so that pulse generator 15 produces an initial single electrical pulse to optical source 11, in addition, pulse generator 15 signals timer 18 to begin its timing mechanism. Upon receiving the single electrical pulse, optical source 11 generates an optical pulse, which propagates through the monitored tissue 14. When the optical pulse reaches detector 12, the detector generates an electrical pulse to amplifier 16 which in turn commands counter 17 to register a pulse revelation and signals pulse generator 15 to generate another single electrical pulse. Thereupon, pulse generator 15 immediately generates a second single pulse to optical source 11 and the process of registering the circulating pulses is repeated. When the number of registered pulse revelations reaches a pre-selected and installed number, counter 17 sends a command to timer 18 to record this time. In the meantime, pulse generator 5 continues to generate pulses for a new measurement sequence. As further described herein, for this technique, the time interval for the circulation of $N_0$ pulses is proportional to the glucose concentration in the tissue and by gauging the changes in the time interval, fluctuations in the individual's glucose concentration can be measured.

The dependence of the time interval t on the glucose concentration in the tissue can be presented as:

$$t(C) = N_0 \cdot \left[ \frac{L \cdot (n_0 + k(\lambda) \cdot C)}{c} + \Delta\tau \right] \quad (7)$$

where, as before, L is the thickness of the monitored tissue, $n_0$ is the refractive index of the tissue without glucose, $k(\lambda)$ is the refractive index sensitivity to glucose concentration, C is the blood glucose concentration, c is the speed of light in vacuum, and $\Delta\tau$ is the time delay in the EPU.

The relationship between the changes in the time of circulation of $N_0$ pulses to blood glucose concentration can be expressed as:

$$\Delta t(C) = t(C) - t(0) = \\ N_0 \cdot \left[ \frac{L \cdot (n_0 + k(\lambda) \cdot C)}{c} + \Delta\tau \right] - N_0 \cdot \left[ \frac{L \cdot n_0}{c} + \Delta\tau \right] = \frac{N_0 \cdot L \cdot k(\lambda)}{c} \cdot C. \quad (8)$$

where t(0) is the time interval required to achieve $N_0$ pulses of circulation when glucose concentration C=0.

Finally, the sensitivity S(C) of the device operating in the time measurement mode to the glucose concentration can be expressed as:

$$S(C) = \frac{d(\Delta t(C))}{dC} = \frac{N_0 \cdot L \cdot k(\lambda)}{c}. \quad (9)$$

As is apparent, the device sensitivity in the time measurement mode is directly proportional to the number of pulse circulation and does not depend on the EPU time delay $\Delta\tau$. It is expected that the glucose monitoring device operating in the time measurement mode will have comparable accuracy and sensitivity as that of the glucose monitoring device configured to operate in the pulse measuring mode as shown in FIG. 1.

The glucose monitoring devices of the present invention can employ a combination of measurements at different wavelengths to compensate for variations in tissue thickness, presence of other blood components such as water during glucose monitoring, and other factors. In this case, the system can employ a single broadband source with appropriate band pass filters and a detector that is capable of detecting radiation at different wavelengths. Alternatively, the system can employ a plurality measurement channels with each channel having a light source and receiver or detector. In either case, the system can use one or several EPUs. For instance, a device can include a first source of radiation having wavelengths in a selected region of the spectrum that is essentially insensitive to fluctuations of glucose but is affected by other factors during glucose monitoring. This first region of the spectrum is called the "reference" region, and the associated detector is called the "reference" detector. The data that is gather either in the pulse measurement mode or the time measurement mode is, therefore, primarily dependent upon the factors other than the concentration of glucose in the tissue.

A second source of radiation generates radiation having wavelengths in a selected region of the spectrum that is strongly affect by glucose levels but not to other factor (or is only very weakly affected by fluctuation these other factors) during glucose monitoring. This second region of the spectrum is called the "measurement" region, and the associated detector is called the "measurement" detector. The data that is gathered either in the number of pulse circulation measurement mode or the time measurement mode is, therefore, primarily dependent upon the concentration of glucose in the tissue.

Each of the reference and measurement sources and detectors will generate data regarding changes in pulse circulation frequency or changes in time of circulation of $N_0$ pulses, and the ratio (or difference) of the data will provide an indication of the glucose content in the tissue. Moreover, because the reference and measure signals are subject to the same major sources of error, e.g., background changes, the ratio or difference data will provide a highly accurate indication of the amount of glucose present.

In addition to measuring glucose, the device can also be designed to monitor other analytes by selected the appropriate wavelength for the measurement source and detector. These analytes include, for example, cholesterol, triglycerides, urea, amino acids, and proteins, e.g., albumin and enzymes. Moreover, the device can be designed to measure a plurality of analytes simultaneously by employing radiation with a plurality of different wavelength regions that are responsive to the analytes being monitor. Most preferably only a single reference optical source that emits radiation at a single wavelength region that is not influenced by the analytes (and the associate reference detector) is used.

Figure 5:
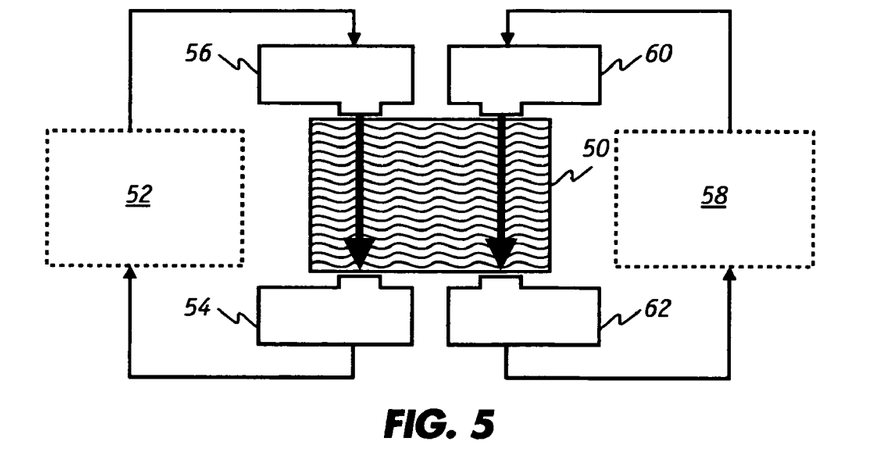

FIG. 5 illustrates another embodiment of the glucose monitoring device that includes two separate EPUs and associated optical sources and detectors to monitor tissue 50. EPU 52 operates optical source 56 that generates a reference radiation and detector 54 and EPU 58 operates optical source 60 that generates a measurement radiation and detector 62. Both EPUs preferably operate in the same measurement mode, i.e., time measurement mode or pulse measurement mode. Alternatively, one can operate in the measurement mode and the other in the pulse measurement mode. Analysis of the combined readings provides an accurate measurement of the glucose concentration of tissue 50 as described above.

Figure 6:
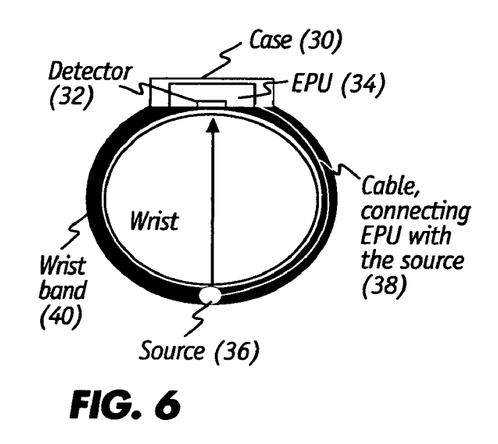
FIG. 6 is a cross-sectional view of a glucose monitoring device when worn on the wrist of an individual.

The glucose monitoring device can be employed to monitor tissue from any part of an individual. A preferred device as shown in FIG. 6 is designed to be worn around the wrist. The device includes an EPU 34 and associated optical source 36 and detector 32. The EPU 34 and detector 32 are enshrouded in a protective case or housing 30 while optical source 36 is attached to an adjustable wrist band 40. Wrist band 40 is worn so that detector 32 and optical source 36 are preferably on direct opposite sides of the wrist so that radiation emitted from optical source 36 is received by detector 32 after passing through the tissue. Optical source 36 is connected to EPU 34 via cable 38 that is embedded in wrist band 40.

Figure 7:
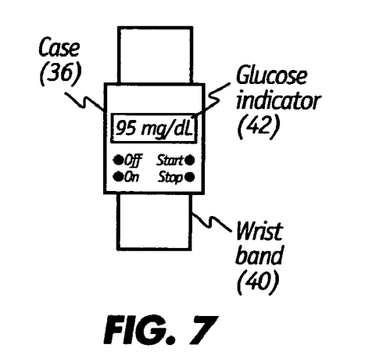
FIG. 7 depicts the glucose monitoring device with the display panel.
Figure 8:
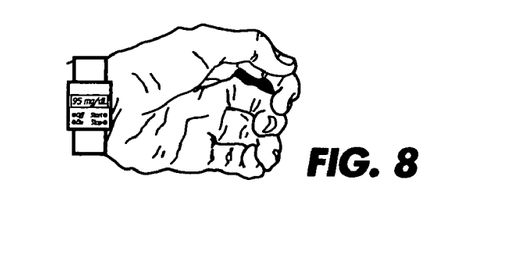
FIG. 8 depicts the glucose monitoring device as worn on the wrist.

As shown in FIGS. 7 and 8, the glucose monitor device can also include a liquid crystal display unit with a glucose indicator 42 on the face of case surface 36. The display unit can also comprise a printer, a display screen, or a magnetic or optical recording device. For individuals who have serious diabetic conditions, the display unit can include a control apparatus that regulates an insulin pump or similar infusion device that is worn or implanted on the individual's body. When configured to be surgically implanted into a user, for example, at a particular location in the venous system, along the spinal column, in the peritoneal cavity, or other suitable site to deliver an infusion formulation to the user. External infusion pumps, which connect to patients through suitable catheters or similar devices, can also be employed. Implantable devices that supply insulin are described, for example, in U.S. Pat. No. 6,122,536 to Sun et al. and U.S. Patent Publication No. 2004/0204673 to Flaherty, U.S. Pat. No. 7,024,245 to Lebel et al, 6,827,702 to Lebel et al., U.S. Pat. No. 6,427,088 to Bowman et al., and U.S. Pat. No. 5,741,211 to Renirie et al., which are incorporated herein by reference.

Figure 9:
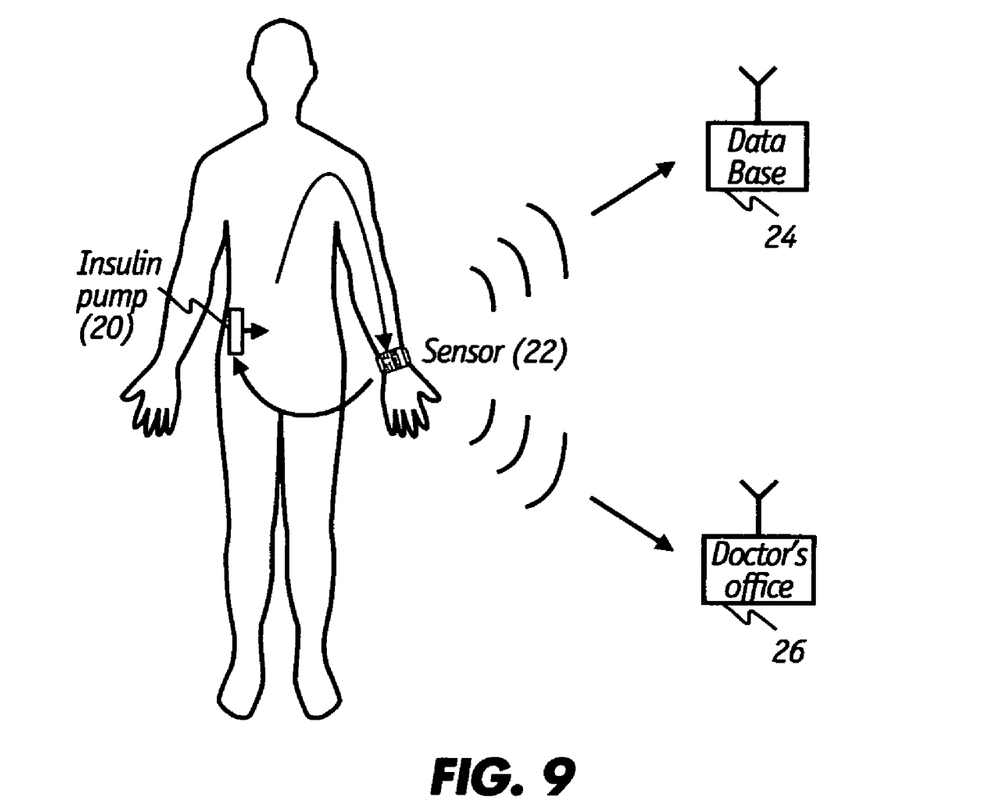
FIG. 9 illustrates the operation of the glucose monitoring device transmitting data and regulating an insulin pump.

As shown in FIG. 9, an insulin pump 20 responds to signals transmitted from a glucose monitoring device 22 to control the administration of insulin. For example, the glucose monitoring device can be equipped with a control circuit that generates a control signal, such as a radio frequency (RF) signal, for remotely controlling the insulin pump 20 which is equipped with an antenna to receive the control signals. The control signals are converted to actuator signals that regulate an actuator driver within the insulin pump 20. Should the measured glucose level of the individual fall below a prescribed threshold, the glucose monitoring device can signal the insulin pump to deliver an appropriate amount of a medical formulation such as an insulin formulation into the individual. The insulin pump 20 can be equipped with an actuator driver that is responsive to the actuator signals and thereby inject an amount of insulin formulation from a reservoir within the insulin pump and into the individual. In addition, glucose monitoring device 22 can transmit signals to a database 24 and doctor's office 26 with a record of the glucose levels.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the following claims.

What is claimed is:

1. A device for noninvasive measurement of the levels of at least one analyte in a subject that comprises:

means for irradiating the subject through tissue with electromagnetic radiation;

means for detecting the radiation that passes through the tissue;

means for calculating the speed at which the electromagnetic radiation passes through the tissue; and means for correlating the calculated speed of the electromagnetic radiation to the concentration of the at least one analyte in the subject.

2. The device of claim 1 wherein the means for irradiating the subject emits pulses of radiation and the means for detecting the radiation measures the number of pulses of radiation that passes through the tissue during a defined time period which is referred as the pulse circulation frequency measurement.

3. The device of claim 2 wherein the means for correlating the calculated speed of the electromagnetic radiation to the concentration of the at least one analyte in the subject calculates the changes, if any, of the pulse circulation frequency being measured.

4. The device of claim 1 wherein the means for irradiating the subject emits pulses of radiation and the means for detecting the radiation measures the time period required for a defined number of pulses of radiation to pass through the tissue which is referred to as the time interval measurement.

5. The device of claim 4 wherein the means for correlating the calculated speed of the electromagnetic radiation to the concentration of the at least one analyte in the subject calculates the changes, if any, of the time interval being measured.

6. The device of claim 1 further comprising means for dispensing a medical formulation in response to a determination of the concentration of the at least one analyte in the subject.

7. The device of claim 1 wherein the at least one analyte is selected from the group consisting of glucose, cholesterol, triglycerides, urea, protein, and mixtures thereof.

8. The device of claim 1 wherein said at least one analyte is glucose.

9. The device of claim 1 wherein the concentration of two or more analytes are measured and the means for irradiating the subject emits electromagnetic radiation at two or more different wavelengths.

10. The device of claim 1 wherein the means for irradiating the subject through tissue with electromagnetic radiation comprises means for irradiating the subject with electromagnetic radiation at different wavelengths and the device further comprises means for detecting the radiation at different wavelengths in order to compensate for variations in conditions other than the concentration of the analyte or analytes being measured.

11. The device of claim 1 wherein the means for irradiating the subject comprises means for supporting the device such that the electromagnetic radiation passes through a defined thickness of the tissue.

12. A device for noninvasive measurement of the levels of glucose in a subject that comprises:

means for irradiating the subject through tissue with electromagnetic radiation having a wavelength such that the speed of the electromagnetic radiation traversing through the tissue is sensitive to the glucose concentration in the tissue;

means for detecting the radiation that passes through the tissue;

means for calculating the speed at which the electromagnetic radiation passes through the tissue; and means for correlating the calculated speed of the electromagnetic radiation to the concentration of glucose in the subject.

13. The device of claim 12 wherein the means for irradiating the subject emits pulses of radiation and the means for detecting the radiation measures the number of pulses of radiation that passes through the tissue during a defined time period, which is referred as the pulse circulation frequency being measured.

14. The device of claim 13 wherein means for correlating the calculated speed of the electromagnetic radiation to the concentration of the glucose in the subject calculates the changes, if any, of the pulse circulation frequency measurement.

15. The device of claim 12 wherein the means for irradiating the subject emits pulses of radiation and the means for detecting the radiation measures the time period required for a defined number of pulses of radiation to pass through the tissue which is referred to as the time interval measurement.

16. The device of claim 15 wherein the means for correlating the calculated speed of the electromagnetic radiation to the concentration of glucose in the subject calculates the changes, if any, of the time interval being measured.

17. The device of claim 12 further comprising means for dispensing an insulin formulation in response to a determination of the concentration of the glucose in the subject.

18. A noninvasive method of monitoring the levels of at least one analyte in a subject that comprises:
  (a) irradiating the subject through tissue of known thickness with electromagnetic radiation;
  (b) detecting the radiation that passes through the tissue in a transmissive mode;
  (c) calculating the speed at which the electromagnetic radiation passes through the tissue; and
  (d) correlating the calculated speed of the electromagnetic radiation to the concentration of the at least one analyte in the subject.

19. The method of claim 18 wherein step (a) comprises directing pulses of radiation through the tissue and step (b) comprises detecting the number of pulses that passes through the tissue during a defined time period, which is referred as the pulse circulation frequency measurement.

20. The method of claim 19 wherein step (d) comprises calculating the changes, if any, of the pulse circulation frequency being measured.

21. The method of claim 18 wherein step (a) comprises directing pulses of radiation and step (b) comprises measuring the time period required for a defined number of pulses of radiation to pass through the tissue which is referred to as the time interval measurement.

22. The method of claim 21 wherein step (d) comprises calculating the changes, if any, of the time interval being measured.

23. The method of claim 18 further comprising the step of dispensing a medical formulation in response to a determination of the concentration of the at least one analyte in the subject.

24. The method of claim 18 wherein the at least one analyte is selected from the group consisting of glucose, cholesterol, triglycerides, urea, protein, and mixtures thereof.

25. The method of claim 18 wherein said at least one analyte is glucose.

26. The method of claim 18 wherein the concentration of two or more different analytes are measured and step (a) comprises irradiating the subject with electromagnetic radiation at two or more different wavelengths.

27. The method of claim 18 wherein step (a) comprises irradiating the subject through tissue with electromagnetic radiation at different wavelengths in order to compensate for variations in conditions other than the concentration of the analyte or analytes being monitored.

* * * * *